(12) United States Patent
Pfeiffer et al.

(10) Patent No.: US 9,194,852 B2
(45) Date of Patent: Nov. 24, 2015

(54) METHOD AND APPARATUS FOR ACCELERATING THE EQUILIBRATION OF A FLUID

(71) Applicant: Roche Diagnostics Operations, Inc., Indianapolis, IN (US)

(72) Inventors: Christoph Pfeiffer, Leobersdorf (AT); Wolfgang Hofmann, Graz (AT); Horst Ruether, Hart bei Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/551,758

(22) Filed: Nov. 24, 2014

(65) Prior Publication Data

US 2015/0079685 A1 Mar. 19, 2015

Related U.S. Application Data

(63) Continuation of application No. PCT/EP2013/060173, filed on May 16, 2013.

(30) Foreign Application Priority Data

May 31, 2012 (EP) .................................. 12170284

(51) Int. Cl.
*G01N 33/49* (2006.01)
*G01N 33/50* (2006.01)
(Continued)

(52) U.S. Cl.
CPC ........ *G01N 33/0006* (2013.01); *B01F 11/0022* (2013.01); *B01F 11/0034* (2013.01);
(Continued)

(58) Field of Classification Search
CPC .. B01F 11/00; B01F 11/0022; B01F 11/0034; B01F 11/004; G01N 33/0006; G01N 33/49; G01N 33/492; G01N 33/4925; Y10T 436/10; Y10T 436/102499; Y10T 436/20; Y10T 436/204998; Y10T 436/207497; Y10T 436/209163; Y10T 436/25875
USPC ........... 436/8, 11, 63, 68, 127, 133, 136, 138, 436/181; 422/68.1, 554, 555; 73/1.01, 1.02, 73/1.03, 1.06
See application file for complete search history.

(56) References Cited

U.S. PATENT DOCUMENTS 3,681,255 A 8/1972 Wilfore
3,849,070 A * 11/1974 Garza et al. ................... 436/133
(Continued)

FOREIGN PATENT DOCUMENTS

EP 2077452 B1 11/2010
WO 2010/018394 A1 2/2010

OTHER PUBLICATIONS

International Search Report issued Jun. 11, 2013, in Application No. PCT/EP2013/060173, 3 pages.
(Continued)

*Primary Examiner* — Maureen Wallenhorst
(74) *Attorney, Agent, or Firm* — Roche Diagnostics Operations, Inc.

(57) ABSTRACT

A method and an apparatus for accelerating the equilibration of a fluid, typically the reference fluid of an analyzer, are provided, the surface of the fluid being in contact with a gas phase. The device can include a cassette, which can be exchangeably inserted into an analyzer and which holds at least one flexible, gas-tight bag, in which the fluid and the gas phase are accommodated. The cassette or the analyzer can include at least one transmitting element, which can be caused to vibrate and which mechanically contacts the flexible bag in order to input mechanical energy into the liquid in at least one wall region.

20 Claims, 7 Drawing Sheets

(51) Int. Cl.
  *G01N 33/00* (2006.01)
  *B01F 11/00* (2006.01)

(52) U.S. Cl.
  CPC ... *G01N33/4925* (2013.01); *Y10T 436/102499* (2015.01); *Y10T 436/209163* (2015.01); *Y10T 436/25875* (2015.01)

(56) References Cited

U.S. PATENT DOCUMENTS

| | | | |
|---|---|---|---|
| 4,116,336 A | | 9/1978 | Sorensen et al. |
| 4,871,439 A | | 10/1989 | Enzer et al. |
| 5,023,186 A | | 6/1991 | Herring |
| 5,230,427 A | * | 7/1993 | Betts et al. ............... 206/213.1 |
| 5,605,664 A | * | 2/1997 | Lauks et al. .................... 422/83 |
| 5,780,302 A | | 7/1998 | Conlon et al. |
| 5,882,602 A | * | 3/1999 | Savage et al. ................. 422/537 |
| 6,405,872 B1 | | 6/2002 | Ruether et al. |
| 7,188,993 B1 | | 3/2007 | Howe et al. |
| 7,378,006 B2 | | 5/2008 | Shin et al. |
| 2009/0176314 A1 | * | 7/2009 | Steinboeck et al. .......... 436/174 |
| 2011/0065084 A1 | | 3/2011 | Rao et al. |

OTHER PUBLICATIONS

Kilani, Jacem and Lebault, Jean-Michel, "Study of the oxygen transfer in a disposable flexible bioreactor with surface aeration in vibrated medium," Applied Microbiology & Biotechnology, 2007, pp. 324-330, vol. 74, Issue 2.

* cited by examiner

METHOD AND APPARATUS FOR ACCELERATING THE EQUILIBRATION OF A FLUID

CROSS-REFERENCE TO RELATED APPLICATIONS

This application is a continuation of International Application No. PCT/EP2013/060173, filed 16 May 2013, which claims the benefit of European Patent Application No. 12170284.9, filed 31 May 2012, the disclosures of which are hereby incorporated by reference in their entirety.

BACKGROUND

Calibration of blood gas analyzers or their sensors is carried out at predetermined time intervals, using calibration fluids that are kept in the analyzer in disposable containers. The amount of fluid held in these containers is usually sufficient for a multitude of calibration measurements.

Quality control of blood gas analyzers requires measurement of control fluids at regular intervals. Comparing the obtained measurement values with the target values for the analytes $O_2$, $CO_2$, pH, etc. of the control fluid will permit evaluation of the quality of the sensors and the measurement system. In general each control measurement uses one ampoule of control fluid. As a consequence, quality controls are cost-intensive. It is therefore desirable to provide containers from which control fluid can repeatedly be aspired and measured.

Although only the values of the analytes in the respective fluids are relevant for calibration or control measurements, the provisions for storage and delivery of these fluids are of primary importance. This is particularly true for the analyte values in blood gas analysis, since these are based on the concentrations of gases dissolved in the fluid ($CO_2$, $O_2$). Gases dissolved in the fluid undergo an exchange with the gas phase contacting the fluid in accordance with Henry's law. A reference fluid stored in a container, which is not sealed gas-tightly and thus is in contact with the ambient atmosphere, will unavoidably suffer a change in analyte values as time passes.

U.S. Pat. No. 3,681,255 (Wilfore) and U.S. Pat. No. 4,871,439 (Enzer et al.) disclose designs of "headspace-free" bags for the storage of calibration and control fluids. The fluids are filled into gas-tight, flexible bags without a gas phase, avoiding the formation of gas bubbles. An exchange between the dissolved gases and a gas phase is thus inhibited. Multiple withdrawal of great amounts of fluid during operation over time does not pose a problem, since the bags are connected to the fittings of the analyzer via tubes and successive withdrawals of fluid will only cause a decrease in volume of the flexible bags.

The above design has the disadvantage that oxygen is not sufficiently stabilized. Since only a small amount of oxygen is dissolved in the aqueous fluid, even a slight decrease of oxygen in the fluid causes a large change in the analyte value for the blood gas parameter $pO_2$, and no stable or predictable target value for this parameter can be ensured over the storage period of the container. A loss of small amounts of oxygen in the solution occurs for instance through reaction of oxygen either with plastic coating material or with substances in the solution with which oxygen reacts as time passes. A further cause for the decrease in oxygen content is slow diffusion through the seams of the container.

Solutions of the stabilization problem of oxygen in headspace-free bags are described in U.S. Pat. No. 4,116,336 (Sorensen et al.), U.S. Pat. No. 5,780,302 (Conlon et al.), and U.S. Pat. No. 7,378,006 (Shin et al.).

U.S. Pat. No. 5,780,302 describes a method for stabilizing $O_2$ by means of packaging the solution in a container made of a laminate. The laminate consists of (a) an inner layer (heat sealable polymer consisting of polypropylene), (b) an intermediate layer (aluminum), (c) an outer layer (polyester nylon and a lacquer coating), and (d) an access device which is located entirely within the container.

U.S. Pat. No. 7,378,006 discloses the addition of choline to the fluid for the stabilizing of $pO_2$ values.

U.S. Pat. No. 6,405,872 (Ruether et al.) proposes for multiple withdrawal of tonometered gas-equilibrated fluids the use of gas-tight, flexible containers with a gas phase acting as a gas reservoir for stabilizing the gas values. The container is connected to the fittings of the analyzer via a line. A disadvantage of this proposal is the fact that, depending on the size of the container and due to the physical circumstances mentioned above, the (new) equilibration following rapid temperature or pressure changes will be slow and require some hours.

A concept for the stabilization of oxygen in control fluids, which are contained in glass ampoules, is based on contact of the fluid with a gas phase within the ampoule. The large amount of oxygen in the gas phase stabilizes the comparatively lower and therefore sensitive oxygen content in a purely aqueous or saline control fluid. A disadvantage of such a gas phase is that the oxygen content of the solution is temperature-sensitive due to the temperature dependence of Henry's constant. The equilibrium distribution of the individual components between gas phase and solution at various temperatures can be computed for small volumes in glass ampoules and can also be found by experiment. Based on the equilibrium distribution target values can be predicted for the blood gas parameters. In known ampoules the volumes of fluid and gas phase are roughly equal and there exists relative to the fluid volume a large phase boundary surface, which due to the rigidity of the vertically standing ampoule is constant. This will provide sufficient predictability of the effective gas values even when temperature changes. The use of ampoules has the economic disadvantage that one whole ampoule is needed for each QC or control measurement, because after opening of the ampoule the gas values will rapidly change due to interaction with the ambient atmosphere.

In contrast to the conditions prevailing if small, rigid ampoules of 1-2 ml content are used as mentioned above, in larger amounts of fluid the equilibrium distribution will take several hours to readjust itself. In the case of fluid volumes of 150 to 300 ml and a surface of 15 $cm^2$ (i.e., a head of liquid of 10-20 cm) the equilibration time or readjustment time, that is the time needed to establish a sufficiently accurate homogeneous distribution of gas concentrations within the fluid after rapid changes of temperature or pressure, lies in the vicinity of 36 hours. After inserting a new container of reference fluids into the analyzer or after prolonged stand-by periods of the analyzer under instable temperature conditions there will result delays in operation or measurement errors.

Cartridges comprising one or more gastight containers, for instance bags made of gas-impermeable plastic material, which are exchangably inserted into the analyzer, present an obvious choice for calibration or control fluids (reference fluids).

It is however necessary to stabilize the oxygen dissolved in the fluid, which serves as target value or analyte for the parameter of oxygen partial pressure ($pO_2$) present in the calibration or control fluid.

As mentioned above this can be achieved by including a gas space (head space) in the bag. The large amount of oxygen in the gas phase stabilizes the comparatively lower and thus more sensitive oxygen content of a purely aqueous or saline control fluid. Due to the temperature dependence of Henry's constant a certain temperature sensitivity of the oxygen content of the solution must be allowed for, however. This is counterbalanced insofar as the gas exchange between aqueous solution and gas phase is purely diffusion based and equilibrium is attained only after a period of some hours, in contrast to the situation given in small ampoules as mentioned above.

Flexible containers include the bags as described in U.S. Pat. No. 6,405,872. These bags consist of a multilayer, gas-tight sheet material that is welded at the edges. Past experience has shown that very good storage stability of reference fluids filled into such bags can be achieved by using a simple commercially available aluminium laminate with polyethylene coating.

In the flexible bags according to U.S. Pat. No. 6,405,872 a first part of volume is occupied by the tonometered fluid containing at least one dissolved gas component. A second part of volume of the flexible bag is provided for the gas phase, which comprises at least the gas component dissolved in the fluid. The surface of the fluid separates the gas phase from the fluid and acts as an exchange surface. Since the volume occupied by the fluid plus the volume of the gas phase together is less than the maximum filling volume of the flexible bag, the interior pressure in the bag equals the ambient atmospheric pressure, even when temperature and pressure changes occur (within predetermined limits).

According to European Patent No. 2 077 452 B1, fluid withdrawal from the flexible bag may be performed with the use of a multi-way valve with at least two valve positions controlled by the analyzer, which may be provided at the entry point of the corresponding connecting line into the bag. The first valve position establishes a connection between the connecting line to the analyzer and the flexible bag while the second valve position closes the flexible bag and establishes a flow connection between an air source, e.g., ambient air and the connecting line.

U.S. Pat. No. 7,188,993 B1 (Howe et al.) discloses a method and apparatus for resonant vibration mixing of fluids, solid particles and/or gases. The apparatus has three independently movable massive bodies connected by spring systems in a rigid housing, where one of these massive bodies, i.e., the oscillator body, is induced to vibrate by an electric motor. A mixing chamber receiving the substances to be mixed is attached to one of the other bodies. An embodiment of the invention describes the use of the apparatus for creating a mixture of a fluid and a gas to produce gasified media, in which the gas is stored in the fluid for a period of time in the form of microsized bubbles. Due to the creation of bubbles in the fluid such methods are not suitable for accelerating equilibration of reference fluids of an analyzer.

U.S. Patent Application Publication No. 2011/0065084 A1 (Rao et al.) discloses a system and a method for the measuring and controlling of oxygen in a rigid-walled culture vessel containing cells in a culture medium and a gas phase. To the interior wall of the culture vessel is attached an optical oxygen sensor in contact with the culture medium, which is externally excited by a light source and monitored by a photodetector whose signal is fed to a control unit. On the outer wall of the culture vessel there is attached a vibration mixer, which imparts vibration energy to the rigid-walled culture vessel based on the feedback of the oxygen sensor. Thus oxygen transport is increased and fast equilibration between culture medium and the gas phase is attained.

SUMMARY

It is against the above background that the embodiments of the present disclosure provide certain unobvious advantages and advancements over the prior art. In particular, the inventors have recognized a need for improvements in methods and apparatus for accelerating the equilibration of a fluid.

The present disclosure provides a method and an apparatus for accelerating the equilibration of a fluid, typically the reference fluid of an analyzer, whose surface is in contact with a gas phase (for instance as a reservoir of $O_2$, which is dissolved in the aqueous solution only in significantly lower concentration), where fluid and gas phase are contained in a flexible bag, and where one or more bags are typically held in a cartridge that can be exchangeably inserted into the analyzer.

Although the embodiments of the present disclosure are not limited to specific advantages or functionality, it is noted that the present disclosure proposes that the energy of mechanical oscillation of an actuator element is imparted to the fluid present in the flexible bag, the input occurring via at least one wall area of the flexible bag, which is in contact with the actuator element. This approach of the disclosure can significantly reduce the equilibration time of the gas values or of the values of the individual reference fluids dependent on the gas values, thus clearly accelerating measuring operation.

In accordance with one embodiment of the disclosure, a method for accelerating the equilibration of a fluid, typically a reference fluid of an analyzer, is provided, the surface of the fluid being in contact with a gas phase and the fluid and the gas phase being contained in a flexible, gas-tight bag held in a cartridge that can be exchangeably inserted into the analyzer, wherein the energy of a mechanical oscillation of an actuator element is applied to the fluid contained in the flexible bag, the input of mechanical energy being effected via at least one wall area of the flexible bag, which wall area is in contact with the actuator element.

In accordance with another embodiment of the disclosure, an apparatus for accelerating the equilibration of a fluid, typically a reference fluid of an analyzer, is provided, the surface of the fluid being in contact with a gas phase, comprising a cartridge, which can be exchangeably inserted into the analyzer and which holds at least one flexible, gas-tight bag containing the fluid and the gas phase, wherein the cartridge or the analyzer is provided with an actuator element that can be brought to oscillate and which is in mechanical contact with at least one wall area of the flexible bag for transmitting mechanical energy into the fluid.

The input of mechanical energy into the fluid typically occurs after a new cartridge has been inserted into the analyzer or after a longer idle period of the analyzer and prior to withdrawal of fluid from the flexible bag. This will ensure for each withdrawal of calibration or control fluid that the gas values are set with sufficient accuracy. A longer idle period (i.e., the time elapsed since the last withdrawal of fluid from the bag) is to be understood as a period of more than one hour.

As an alternative, the input of mechanical energy into the fluid may also take place after significant changes of pressure or temperature at the site where the analyzer is located or operated. A significant pressure change will for instance be an increase or decrease of ambient air pressure by about 10 mbar, or 20 mbar, or even 30 mbar or more. A significant change in temperature will for instance be an increase or decrease of ambient temperature at the location of the analyzer of 1° C., or 2° C., and in particular 3° C. or more.

The procedure according to the disclosure can be carried out especially if a change in pressure or temperature occurs relatively fast, e.g., within a time span of 12 hours.

According to the disclosure mechanical vibrations are applied in a frequency range extending from infrasound (ca., 1 Hz) to 500 Hz, typically 25 Hz to 50 Hz, with an amplitude of 0.5 mm to 5 mm, typically 1 mm to 3 mm.

Particularly good results can be obtained if the mechanical energy is supplied in the form of saw-tooth or trapezoidal oscillations, typically with steep slopes, or as a periodic shock wave.

In the coupling of mechanical energy care should be taken to avoid any resonant excitation.

Resonant excitation of the system will generate surface waves at the phase boundary surface. This will increase the boundary surface but will not induce the desired mixing in the fluid phase. Resonance will furthermore increase the amplitude of the system in such a way that the fluid phase will intermix with the gas phase. This will produce undesirable gas bubbles in the fluid phase.

A variant of the apparatus of the disclosure for accelerating the equilibration of a fluid whose surface is in contact with a gas phase, is characterized in that the cartridge is provided with at least one actuator element, which can be brought to vibrate and which mechanically contacts the flexible bag in at least one wall area.

In an alternative variant of the apparatus of the disclosure for accelerating the equilibration of a fluid whose surface is in contact with a gas phase, the actuator element is integrated in the analyzer and the cartridge has a contact area (e.g., an opening in the cartridge bottom) by which the actuator element of the analyzer can be brought into contact with the flexible bag contained in the cartridge.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

The present disclosure relates to a method and an apparatus for accelerating the equilibration of a fluid, typically a reference fluid of an analyzer, whose liquid surface is in contact with a gas phase, comprising a cartridge that can be exchangeably inserted into the analyzer, the cartridge including at least one flexible, gastight bag containing the fluid and the gas phase.

The reference fluid mentioned is a liquid that is used for quality control or calibration of analyzers for determining, for instance, the parameters $pO_2$, $pCO_2$, pH or other parameters of blood gas measuring by means of blood gas analyzers, where the fluid together with a gas phase is contained in a flexible, gas-tight container.

Equilibration of a fluid, i.e., achieving equilibrium in the fluid, in this context means adjusting the concentrations $c_i$ of the gases dissolved in the fluid to the corresponding partial pressures $p_i$ of the gases in the gas phase, according to Henry's law $$c_i = \alpha_i * p_i$$

where $c_i$ is the concentration of the gas component in the fluid, $p_i$ is the partial pressure of the gas component in the gas phase, and $\alpha_i$ is the temperature-dependent Henry constant of the $i^{th}$ gas phase. In contrast to dissolved gases the temperature-dependent partial pressure of the liquid (e.g., $H_2O$) in the gas phase is obtained from the Clausius-Clapeyron equation. When partial pressures $p_i$ and/or the temperature change, a new equilibrium will result. The total pressure $p_{total}$ prevailing in the gas space of the closed flexible bag is equal to ambient pressure, i.e., to barometric air pressure: $p_{total} = p_{baro}$. The total pressure of the gas phase in turn equals the sum of the partial pressures of the individual gases present in the gas phase (e.g., $N_2$, $O_2$, $CO_2$, $H_2O$), $$p_{total} = \Sigma p_i.$$

Thus, the point of equilibrium and the distribution of the individual gas components (e.g., $N_2$, $O_2$, $CO_2$, $H_2O$) between gas phase and fluid will depend on barometric pressure and temperature. This is the case for $O_2$ and $N_2$, in particular. In aqueous solution $CO_2$ reacts to $H_2CO_3$ and further to $HCO_3^-$, $CO_3^{2-}$, and $H^+$, such that further chemical equilibria are involved. Via the thermodynamic equilibria of dissolved $CO_2$ with $HCO_3^-$, $CO_3^{2-}$, and $H^+$, the pH value of the fluid is indirectly dependent on the $pCO_2$ in the gas phase.

If the flexible bag and the fluid contained therein are at rest, the kinetics of equilibration depends on the transition kinetics of individual components of the gas from the gas space into the fluid and vice versa, and will also depend on the diffusion velocity of the individual gas components within the fluid. The latter is above all the case for gases that under standard conditions do not react with the fluid (e.g., $N_2$ and $O_2$). As regards to $CO_2$, reactions with the aqueous fluid and the pH-relevant substances it contains, must be taken into account.

Thermodynamic equilibrium is attained when the distribution of each individual gas component between gas phase and fluid follows Henry's law and when the concentrations of the individual gas components or their reaction products are uniform over the total fluid volume. A change in barometric pressure, for instance due to weather conditions, causes a change of total pressure $p_{total}$ of the gas phase in the flexible bag and thus leads to a change of the partial pressures $p_i$ of the individual gases and thus to a shift in equilibrium. Since Henry's constant and the gas partial pressure of the fluid are temperature-dependent, temperature changes will have a similar effect. Following each such change mass transport (transport of substance) will occur to achieve a new equilibrium. The time required to attain the new state of equilibrium depends on the geometric relations in the flexible bag and the prevailing ratio of liquid to gas phase. Both conditions will change in particular as fluid is increasingly depleted.

The essential parameters for the kinetics of equilibration are the size of the area of the fluid surface exposed to the gas phase and the length of the diffusion paths of the gas components or their reaction products in the fluid volume.

DEFINITIONS

Analyte
    The analyte or analytes are the substances contained in the sample fluid—e.g., blood, blood plasma, blood serum, or other body fluids—whose presence and/or concentration analysis (measurement) of the sample medium by means of an analyzer is supposed to determine. Such analytes include $O_2$, $CO_2$ and pH-value, for instance.

Analyzer or pH/Blood Gas Analyzer
    In a simple variant an (automated) pH/blood gas analyzer determines oxygen partial pressure ($pO_2$), carbon dioxide partial pressure ($pCO_2$), pH-value and possibly barometric pressure by means of sensors. The total time required for measurement using a sample volume of 50-100 μl whole blood is usually 30-60 seconds. Certain pH/blood gas analyzers additionally measure analytes such as blood electrolytes ($Na^+$, $K^+$, $Ca^{++}$, $Cl^-$), certain metabolites (glucose, lactate, urea and creatinine) and haemoglobin values, and compute further parameters derived therefrom.

Sensors
    Measurements are usually carried out in exchangeable measuring chambers furnished with electrochemical (electrodes) and/or optical (optodes) sensor elements. Also employed in this context are photometric/spectroscopic methods, in which the optical properties of the sample or color reactions are used for determining the analytes.

Equilibration
    Equilibration is to be understood as the establishing of equilibrium between a fluid and a gas phase in direct contact therewith, where the gas phase may comprise a plurality of gases. In equilibrium the net mass transport between fluid and gas phase is zero, and the individual gas components and their reaction products are essentially uniformly distributed in the liquid phase.

Calibration Fluid
    Synonyms are Calibration Medium, Reference Liquid/Solution, Reference Material
    These are aqueous liquids with different, known concentrations of one or more analytes, concentrations lying in the expected range of the variable to be measured. Calibration fluids are used to calibrate the individual sensors and are for instance known from U.S. Pat. No. 4,116,336.

Control Fluid
    Synonyms are Control Liquid, QC-Fluid, Control Solution
    Similar to calibration fluids, control fluids are aqueous liquids with different, known concentrations of one or more analytes lying in the expected range of the variable to be measured. Control fluids are used for quality control of the measuring system or of one or more individual sensors. Such fluids are for instance known from U.S. Pat. No. 4,116,336.

Reference Fluid
    Furtheron, calibration and control fluids will be subsumed under the term reference fluids, when both processes (calibration and control) are referred to. Calibration and control fluids may have essentially identical composition, they differ however in application. Due to technical or regulatory reasons it does not make sense to calibrate a sensor and then control the calibrated sensor with one and the same fluid. If such a procedure were used a number of defects or mistakes (wrong composition of fluid, wrong parameter values, sensor errors, system errors, etc.) might go undetected.

Calibration
    Synonym: Referencing
    User-site calibration is a procedure for determining the characteristic of individual sensors in terms of characteristic parameters. When a sensor is being calibrated it is brought into contact with different calibrating media, which contain the analyte in different, known concentrations.
    To determine the sensor characteristic the sensor signal is measured for a series of aqueous calibrating media containing the analyte to be determined in different, known concentrations distributed over the expected range of the variable to be measured. Using the calibration values obtained the parameters of the sensor characteristic are determined (e.g., offset, slope, signal amplitude, etc).

Quality Control
    Synonym: QC
    For control measurement, or more precisely, quality control (QC measurement) the sensors of the analyzer are brought into contact with one or more control fluids that contain the analyte/analytes with known concentration(s). The actual values obtained from control measurement permit monitoring the performance of the sensors and the system. Actual and target values are compared and depending on the differences observed certain corrective actions are initiated, such as enabling sample measurement, calibration, checking the system, replacement of components, etc.

Figure 1:
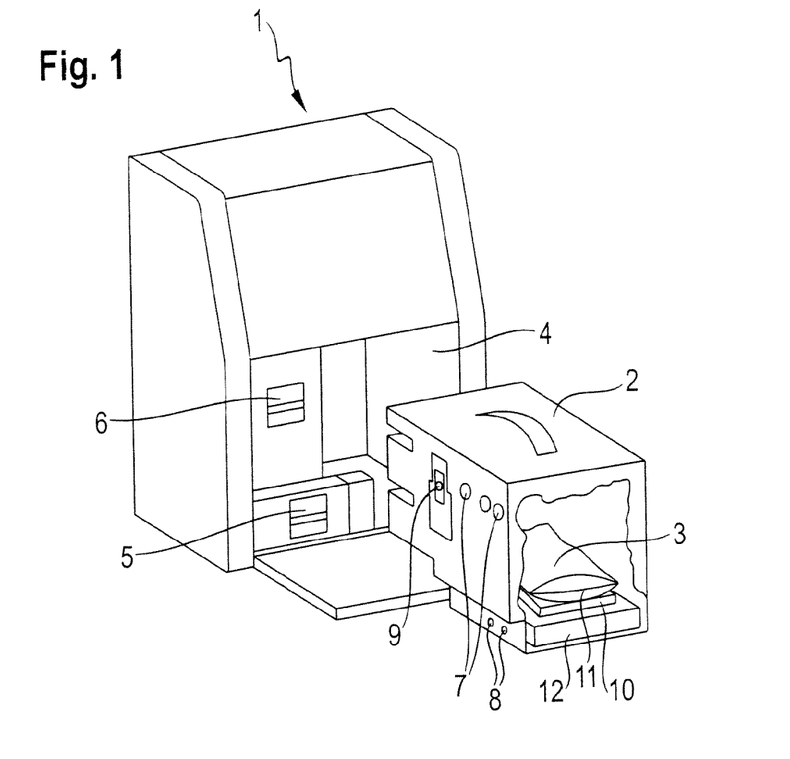
FIG. 1 is an analyzer with an apparatus according to the disclosure for accelerating the equilibration of a fluid, in a three-dimensional view.

FIG. 1 presents a schematic view of an analyzer 1, for instance a blood gas analyzer, where operational and consumable materials may be supplied to the analyzer in the form of one-way cartridges and/or modules.

The cartridge 2 (fluidpack), which can be inserted into a slot 4 of the analyzer 1, houses fluid- and waste containers, in particular gastight bags 3, which contain reference fluids needed for the operation of the analyzer 1, i.e., control fluids for quality control and calibration fluids for calibrating the sensors.

Optionally, control fluids for QC could also be supplied to the analyzer 1 in a separate cartridge 5 and thus could be replaced in a simple way independently of the cartridge 2 holding other reference and operational liquids.

The analyzer 1 furthermore has a sensor cartridge 6 containing at least part of the sensors needed for analyte determination.

Cartridge 2 also comprises connection lines (not shown here) to the flexible bags 3, each leading to a docking nipple 7 at the outer side of the cartridge 2, such that after insertion of cartridge 2 into slot 4 of the analyzer 1 a fluidtight connection with the corresponding fittings of the analyzer will be established automatically. Furthermore, there also may be provided electrical contacts 8 at the outer side of the cartridge 2, which are assigned to corresponding electrical contacts in slot 4.

A storage module 9 is attached to the cartridge 2, for instance a storage chip or an RFID chip carrying information on the reference fluids in the cartridge 2 and their individual target values. This information can be automatically read by the analyzer 1 after insertion of the cartridge 2.

In order to apply mechanical oscillations to the flexible bag 3, the cartridge 2 is provided with at least one actor or actuator element 10, which can be put into oscillatory motion and which contacts at least one flexible bag 3 in at least one wall area 11.

The actuator element 10 is connected to a drive unit 12, which is either housed in the cartridge 2—as shown in FIG. 1—or typically is integrated in the analyzer 1 and remains in the analyzer 1 when the cartridge is replaced.

Figure 2:
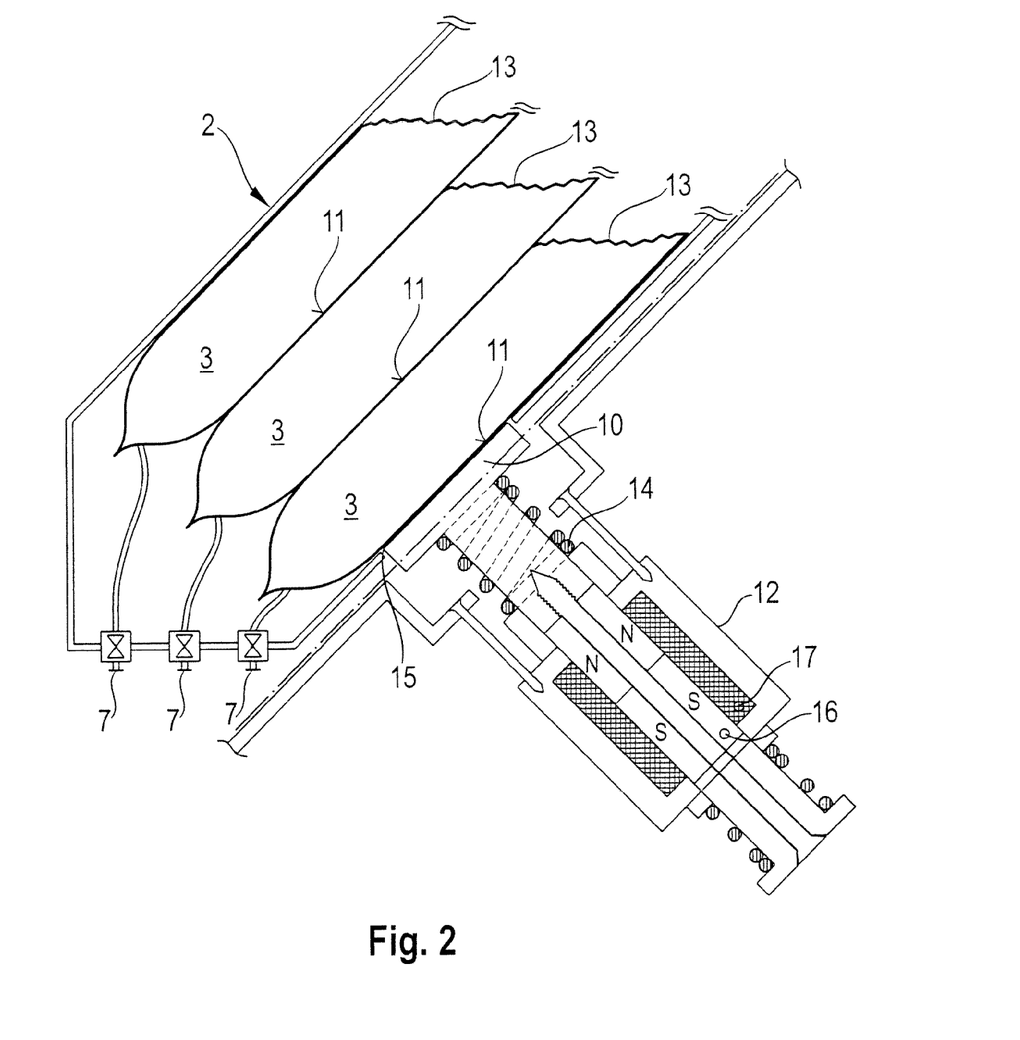
FIG. 2 is a variant of an apparatus according to the disclosure for accelerating the equilibration of a fluid, in a sectional view.

In the variant of an exchangeable cartridge 2 shown in FIG. 2, a number of flexible bags 3 are stacked, the wall areas 11 of the bags 3 being in direct or indirect contact with each other to permit transmission of the vibratory motion. The energy of the mechanical oscillation generated by the actuator element 10 propagates through the first, lowermost bag 3 into the adjacent other bags 3. The fluid surface in the individual flexible bags 3 is indicated by reference numeral 13. The bags 3 are attached to the cartridge 2 at their upper ends (not shown) to keep them from slipping downwards.

The bags 3 may also be connected indirectly, for instance via interposed intermediate layers or separation webs, or by resting on a common carrier, for instance a shelf-shaped holding rack. In the latter case the input of mechanical energy may be effected via the common carrier, which will thus assume the function of the actuator element 10.

As an alternative to FIG. 1, there is shown a variant of the cartridge 2 in FIG. 2, where the actuator element 10 is not part of the cartridge 2 but is an integrated part of the analyzer 1 and in the example shown is connected to the drive unit 12 (with permanent magnet 16 and magnetic coil 17), which also is located in the analyzer, by means of a spring-borne receiving slot. In this variant the cartridge 2 is provided at its bottom with a corresponding opening 15, through which the actuator element 10 of the analyzer may enter the interior of the cartridge 2 during operation and thus mechanically contact the adjacent bag 3 at least in a wall area 11.

The flexible bags 3 can have two essentially rectangular wall areas, which are welded together at their edges (envelope-type bags).

Vertically positioned (envelope-type) flexible bags present a particularly high and slender fluid column with relatively small fluid surface and long diffusion paths. An advantage of this arrangement is that fluid may be easily withdrawn, equilibration time (time to achieve equilibrium) will be longer, however.

Horizontally positioned (envelope-type) flexible bags present a particularly low and wide fluid column with relatively large fluid surface and short diffusion paths. An advantage of this arrangement is that equilibration time (time to achieve equilibrium) is short, but withdrawal of fluid is somewhat encumbered and it may not be possible to completely drain the fluid.

Flexible bags 3, which are held in the cartridge 2 in an oblique position, having an angle against the horizontal plane of 5° to 80°, typically 10° to 50°, are particularly typical (FIG. 2).

The contact area of the actuator element 10 may be 20% to 70%, typically 25% to 50%, of the contact face 11 of the flexible bag 3 in the cartridge 2.

Figure 3:
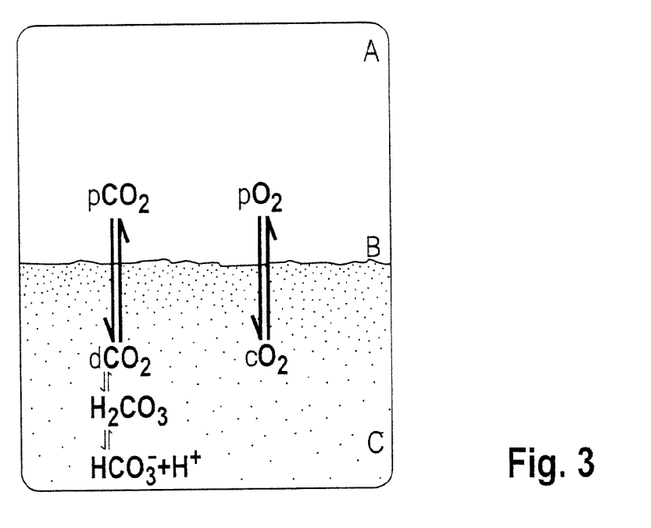
FIG. 3 is a schematic presentation of the processes occurring during equilibration between fluid and gas phase, without input of mechanical energy.
Figure 4:
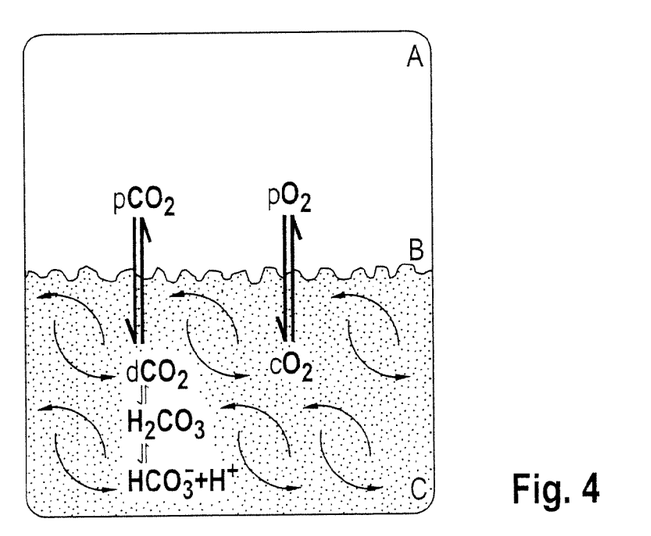
FIG. 4 is a schematic presentation of the processes occurring during equilibration between fluid and gas phase, under input of mechanical energy.

As is illustrated in FIGS. 3 and 4, the approach proposed by the disclosure is based on the idea of forced circulation of the liquid phase in the flexible bag 3 and of enlargement of the interface between gas phase and fluid by means of an input of mechanical energy (vibration). FIG. 3 shows the situation without input of mechanical energy, while FIG. 4 is under input, the following signs being used:

A gas phase (head space)
B phase boundary surface (interface)
C aqueous solution
$pCO_2$ partial pressure of carbon dioxide in the gas phase
$pO_2$ partial pressure of oxygen in the gas phase
$cCO_2$ concentration of dissolved carbon dioxide
$cO_2$ concentration of dissolved oxygen A significant shortening of equilibration time of the blood gas parameters ($pO_2$, $pCO_2$, pH) is observed. This reduction in equilibration time is such that after 60 seconds or less no difference will be found between actual values and target values. Research has been carried out concerning the conditions under which fast equilibration will occur in a system comprising a fluid and a gas phase. The vibration device (FIG. 2) executes a linear motion since the best results will be obtained thereby. As an actuator element 10, a polycarbonate plate may be used, which is attached to the spring-borne receiving slot 14. The magnetic coil 17 of the analyzer-integrated drive unit 12 is driven by a function generator via a power operational amplifier.

Figure 5:
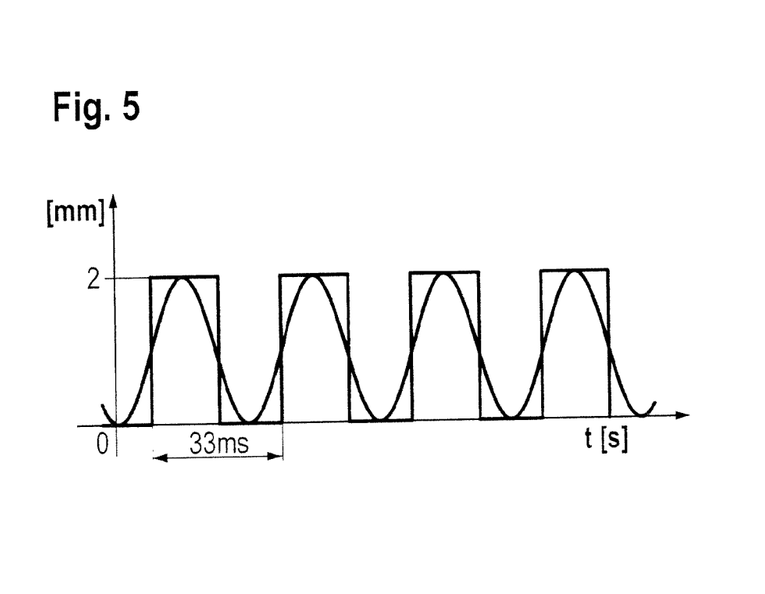
FIG. 5 is a diagram showing possible forms of oscillation used for an actuator element according to an embodiment of the disclosure.

As can be seen from FIG. 5, the disclosure proposes vibrations with curve shapes in a range between purely sinusoidal curves and rectangular curves with steep slopes.

Among possible drive units there are for instance oscillators such as piezoelectric actuators, in particular multi-layer piezo-actuators, motors, in particular eccentrical motors, motors with connection rod coupling, or typically electromagnetic oscillator systems, in particular spring-mass-spring systems.

Oscillations in a frequency range between 1 Hz and 500 Hz, typically 25 Hz to 50 Hz, and with an amplitude from 0.5 mm to 5 mm, typically 1 mm to 3 mm, have been found to be advantageous.

Figures 6, 7:
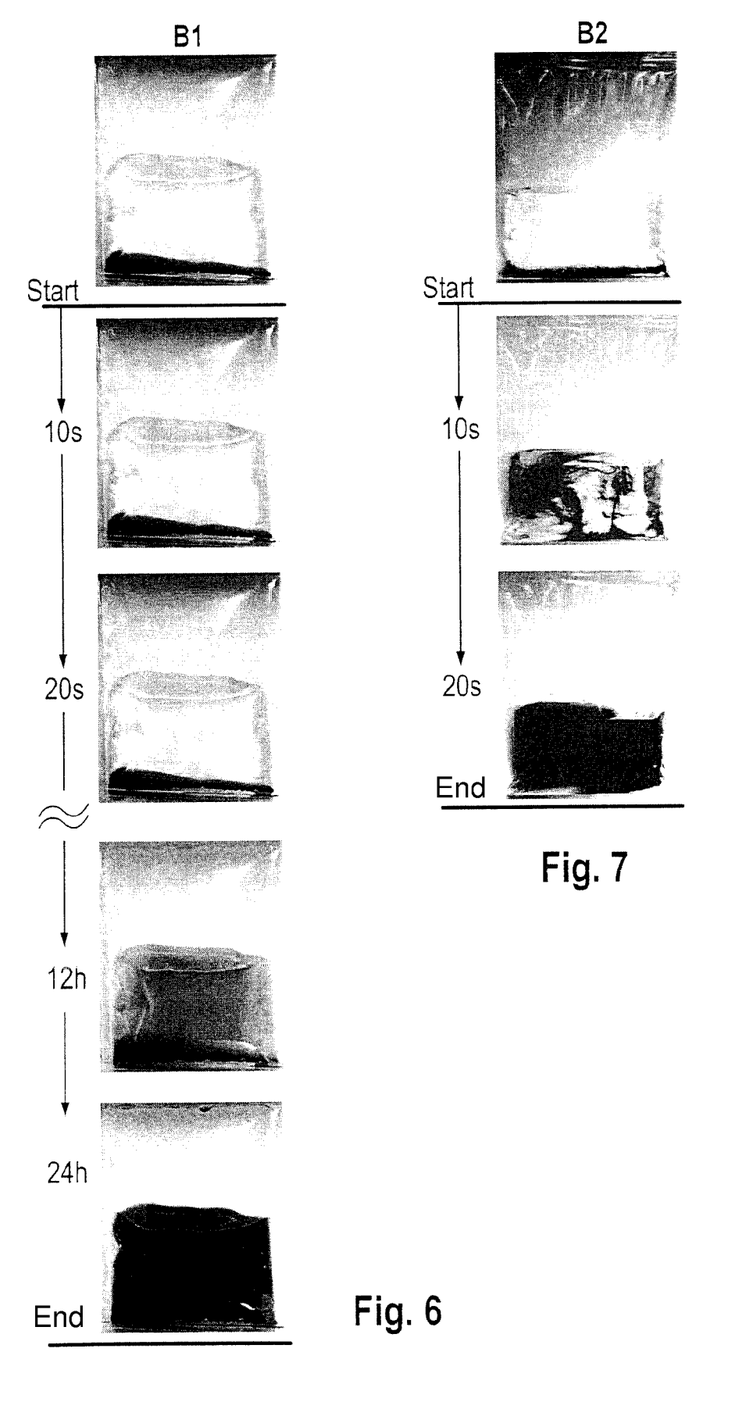
FIG. 6 displays images of an arrangement with a partly filled flexible bag at various points of time, in a state of rest (i.e., without input of mechanical energy)
FIG. 7 displays images of an arrangement with a partly filled flexible bag at various points of time, with input of mechanical energy.

As presented in FIGS. 6 and 7, an experimental set-up using vertically standing envelope-shaped flexible bags with 100 ml fluid and 100 ml gas phase each, will show the improved dynamics in establishing a homogeneous distribution of a substance in a liquid phase. The flexible laminate bags B1 and B2 were each filled with 100 ml pH-buffered salt solution and 100 ml air. Subsequently, 5 ml dye solution were injected into the solutions to form a lower layer. Bag B1 stays at rest and by means of the distribution of the dye simulates the development over time of the diffusion of a substance in the solution. Bag B2 is set into motion by means of the device shown in FIG. 2.

In bag B1 (see FIG. 6) it took 24 hours until no trace of a color gradient could be found anymore, while in bag B2 (see FIG. 7) homogeneous mixture was achieved after 20 seconds. The simulation shows that input of mechanical energy into the bags according to an embodiment of the disclosure will significantly accelerate the mixing within the liquid phase.

Figure 8:
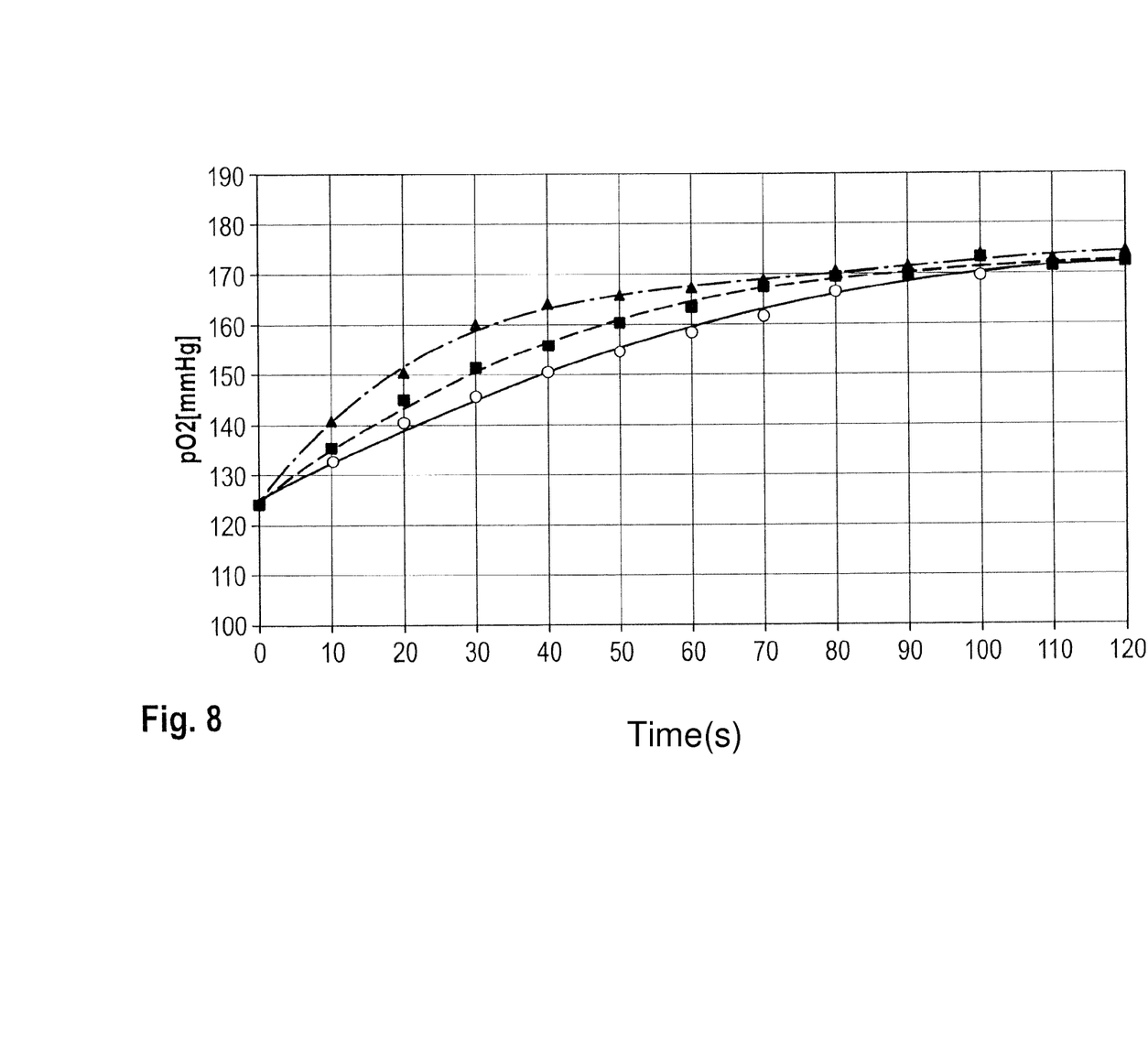
FIG. 8 is a diagram of the equilibration of $O_2$ in a fluid. The three curves refer to a system with three bags as shown in FIG. 2. The triangles refer to the first, lower bag, which is connected to the actuator element, the squares refer to the intermediate bag, the circles to the topmost bag.

FIG. 8 shows the progress of equilibration of $O_2$ in a system as shown in FIG. 2 with three stacked, flexible bags 3.

Into the headspace-free bag containing 100 ml salt solution equilibrated with $O_2$ at 120 mm Hg, 100 ml gas phase (air at 170 mm Hg $O_2$) was injected as headspace by means of a syringe at room temperature (ca., 22° C.). Mechanical energy was coupled in by means of a device analogous to that of FIG. 2 at a frequency of 32 Hz and an amplitude of 1.5 mm. Via a line connected at the lowermost point of the bag, samples were taken at defined intervals of time and the $pO_2$ value was determined by a blood gas analyzer.

It has been found that the bottom bag (triangles), which is in direct contact with the actuator element 10, undergoes fastest equilibration, but that the bags lying above it (squares and circles) are only slightly slower in equilibration, and that after about 90 seconds all three bags are essentially uniformly equilibrated.

Figure 9A:
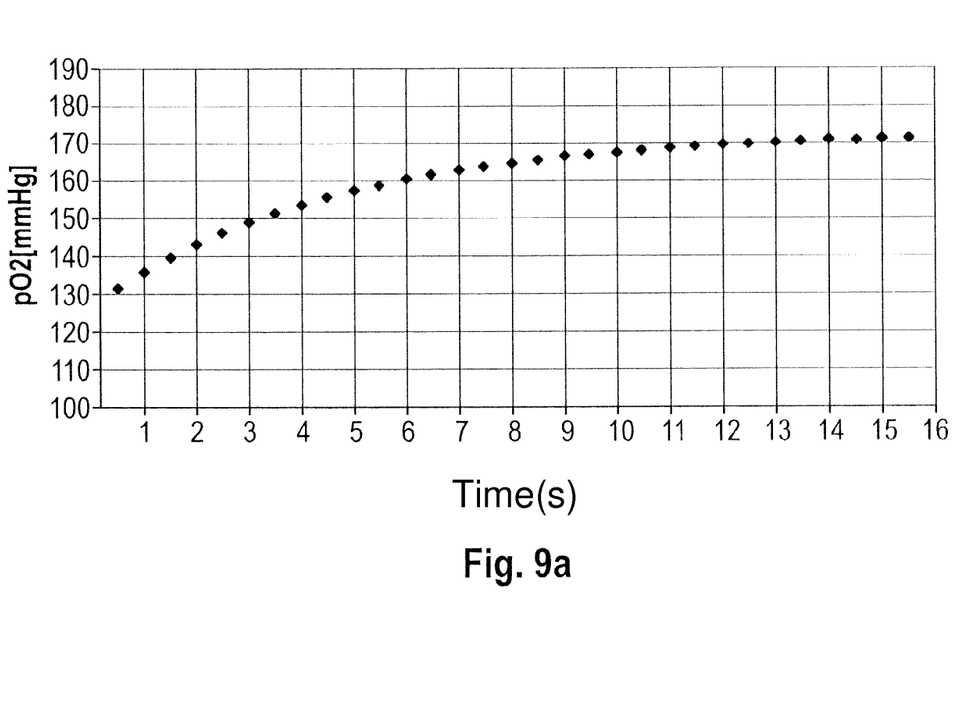
FIGS. 9a and 9b are diagrams of $O_2$-equilibration of a "horizontal" bag (10° slope against the horizontal plane) with (FIG. 9b) and without (FIG. 9a) input of mechanical energy according to the disclosure.
Figure 9B:
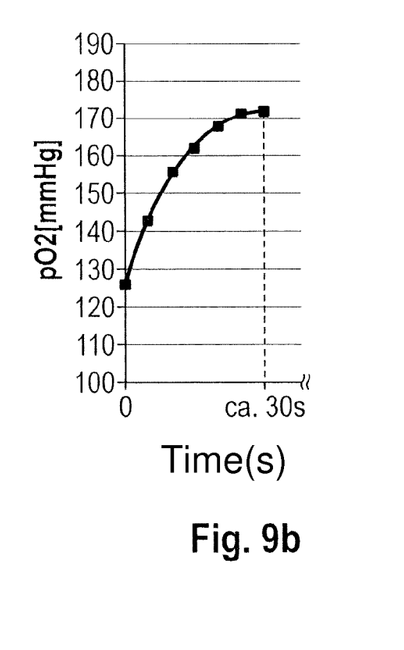

FIG. 9 shows the equilibration of $O_2$ in a horizontal bag (10° slope against the horizontal plane) with and without energy being coupled in as specified by the disclosure. A gas phase of 100 ml (air at 170 mm Hg $O_2$) was injected as head space by means of a syringe at room temperature (ca., 22° C.), into a headspace-free bag containing 100 ml salt solution equilibrated with $O_2$ at 120 mm Hg. Subsequently via a line connected at the lowermost point of the bag, samples were taken at defined intervals of time and the $pO_2$ value was determined by a blood gas analyzer. The time until equilibration was about 15 hours (FIG. 9a). Then the experiment was repeated, with energy coupled in via a device as shown in FIG. 2 at 32 Hz frequency and 1.5 mm oscillation amplitude. The time to equilibration was only 30 seconds (FIG. 9b). For the arrangement of FIG. 9a without input of mechanical energy a $t_{50}$-time (time to reach 50% of the equilibrium value) of 5 hours and a $t_{70}$-time (time to reach 70% of the equilibrium value) of 7 hours was found. For the arrangement of FIG. 9b with input of mechanical energy a significantly lower $t_{50}$-time of 10 seconds and a $t_{70}$-time of 14 seconds was found.

Figure 10A:
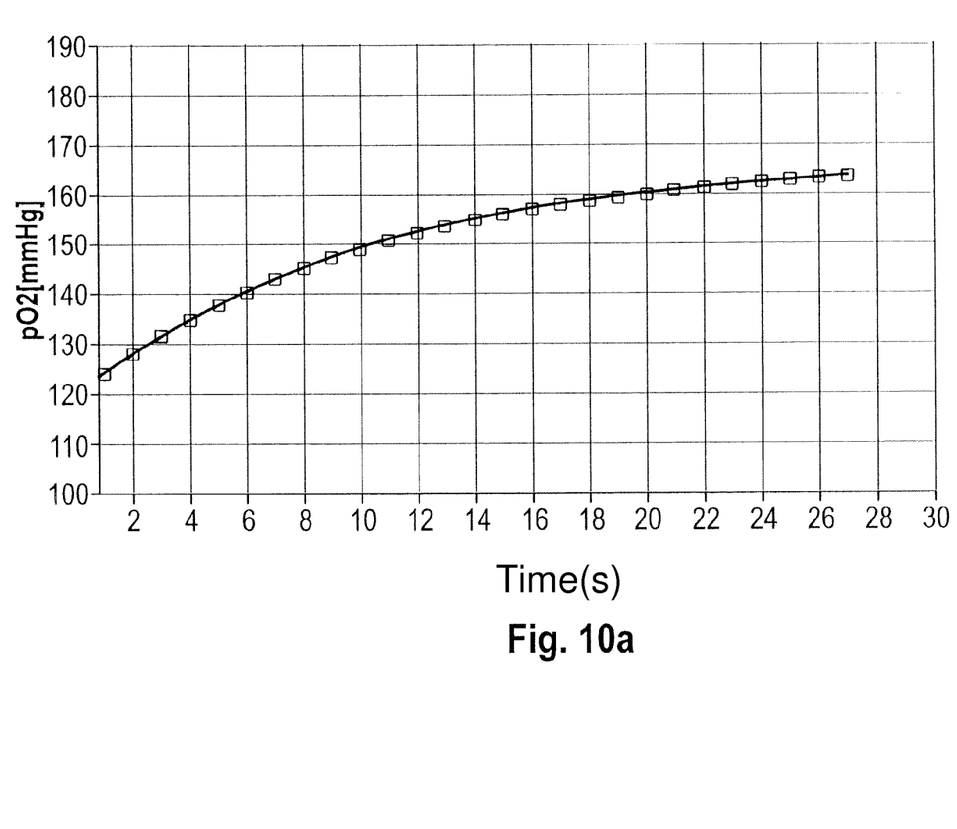
FIGS. 10a and 10b are diagrams of $O_2$-equilibration of a "vertical" bag (80° slope against the horizontal plane) with (FIG. 10b) and without (FIG. 10a) input of mechanical energy according to the disclosure.
Figure 10B:
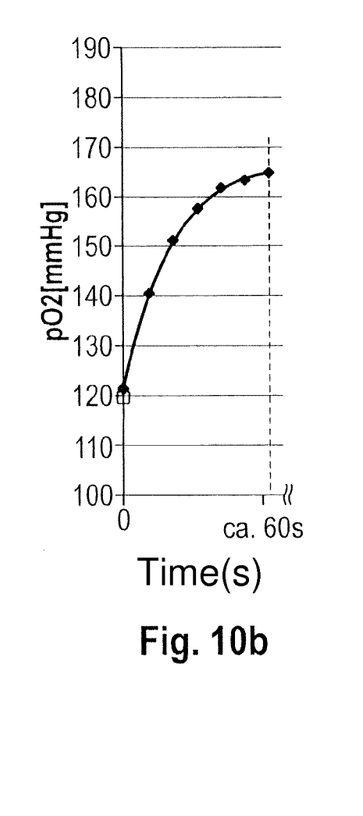

FIG. 10 shows the equilibration of $O_2$ in a vertical bag (ca., 80° slope against the horizontal plane) with and without energy being coupled in as specified by the disclosure. A gas phase of 100 ml (air at 170 mm Hg $O_2$) was injected as head space by means of a syringe at room temperature (ca., 22° C.), into a headspace-free bag containing 100 ml salt solution equilibrated with $O_2$ at 120 mm Hg. Subsequently via a line connected at the lowermost point of the bag, samples were taken at defined intervals of time and the $pO_2$ value was determined by a blood gas analyzer. The time until equilibration was about 26 hours (FIG. 10a). Then the experiment was repeated, with energy coupled in via a device as shown in FIG. 2 at 32 Hz frequency and 1.5 mm oscillation amplitude. The time until equilibration was approximately 60 seconds (FIG. 10b). For the arrangement of FIG. 10a without input of mechanical energy a $t_{50}$-time of 7 hours and a $t_{70}$-time of 13 hours was found. For the arrangement of FIG. 10b with input of mechanical energy a significantly lower $t_{50}$-time of 15 seconds and a $t_{70}$-time of 24 seconds was found.

The operational temperature of the fluid in the bag is usually equal to or slightly above room temperature.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value measurement, or other representation. These terms are also utilized herein to represent the degree by which a quantitative representation may vary from a stated reference without resulting in a change in the basic function of the subject matter at hand.

It will be apparent to those skilled in the art that various modifications and variations can be made to the embodiments described herein without departing from the spirit and scope of the claimed subject matter. Thus, it is intended that the specification cover the modifications and variations of the various embodiments described herein, provided such modifications and variations come within the scope of the appended claims and their equivalents.

What is claimed is:

1. A method of accelerating the equilibration of a reference fluid for a blood gas analyzer, comprising the steps of:
   supplying a reference fluid in a gas-tight, flexible bag, housed in a cartridge, the reference fluid having a gas phase and a liquid phase;
   inserting the cartridge into the blood gas analyzer; and
   applying mechanical oscillation by means of an actuator in contact with a surface of the gas-tight, flexible bag, wherein the mechanical oscillation does not cause resonant vibration of the reference fluid.

2. The method of claim 1, wherein the actuator is separate from the cartridge.

3. The method of claim 1, wherein the actuator is integrated with the cartridge.

4. The method of claim 1, wherein the mechanical oscillation frequency is from about 1 Hz to about 500 Hz.

5. The method of claim 4, wherein the mechanical oscillation frequency is from about 25 Hz to about 50 Hz.

6. The method of claim 1, wherein the mechanical oscillation amplitude is from about 0.5 mm to about 5 mm.

7. The method of claim 6, wherein the mechanical oscillation amplitude is from about 1 mm to about 3 mm.

8. The method of claim 1, wherein multiple gas-tight, flexible bags are housed in the cartridge, those bags being adjacent to one another, each bag having a reference fluid with a gas phase and a liquid phase, and the actuator in contact with the surface of one of the bags.

9. The method of claim 1, wherein the form of oscillation by the actuator ranges from sinusoidal to rectangular.

10. The method of claim 9, wherein the oscillation form is saw-tooth or trapezoidal.

11. The method of claim 9, wherein the mechanical oscillation amplitude is from about 0.5 mm to about 5 mm and the oscillation frequency is from about 1 Hz to about 500 Hz.

12. The method of claim 9, wherein the mechanical oscillation amplitude is from about 1 mm to about 3 mm, and the mechanical frequency is from about 25 Hz to about 50 Hz.

13. The method of claim 1, wherein the contact area of actuator to flexible bag is from about 20% to about 70% of the area of a wall of the bag.

14. The method of claim 1, wherein the mechanical oscillator frequency is from about 1 Hz to about 500 Hz, and the mechanical oscillation amplitude is from about 0.5 mm to about 5 mm.

15. An apparatus for accelerating the equilibration of a reference fluid for a blood gas analyzer, comprising:
- a blood gas analyzer;
- a cartridge that can be exchangeably inserted into the blood gas analyzer and that houses a reference fluid in a gas-tight, flexible bag, the reference fluid having a gas phase and a liquid phase; and
- an actuator element connected to a drive unit for mechanical oscillation of a wall of the gas-tight flexible bag.

16. The apparatus of claim 15, wherein the cartridge houses multiple gas-tight flexible bags, those bags being adjacent to one another, each bag having a reference fluid with a gas phase and a liquid phase, the bags being positioned in the cartridge so that the actuator element is capable of contacting a wall of one of the bags.

17. The apparatus of claim 15, wherein the gas-tight flexible bag is held in the cartridge in oblique position against the horizontal plane.

18. The apparatus of claim 17, wherein the oblique position is inclined from about 5° to about 80° against the horizontal plane.

19. The apparatus of claim 18, wherein the contact area of the actuator element to flexible bag is from about 20% to about 70% of the area of a wall of the flexible bag.

20. The apparatus of claim 19, wherein the cartridge houses multiple gas-tight, flexible bags, those bags being adjacent to one another, each bag having a reference fluid with a gas phase and a liquid phase, the bags being positioned in the cartridge so that the actuator element is capable of contacting a wall of one of the bags.

* * * * *